United States Patent
Bacqué et al.

(10) Patent No.: US 6,806,277 B2
(45) Date of Patent: Oct. 19, 2004

(54) QUINOLYLPROPYLPIPERIDINE DERIVATIVES, PREPARATION PROCESS AND INTERMEDIATES, AND COMPOSITIONS INCLUDING THEM

(75) Inventors: Eric Bacqué, Gif sur Yvette (FR); Jean-Luc Malleron, Marcoussis (FR); Serge Mignani, Chatenay Malabry (FR); Michel Tabart, La Norville (FR)

(73) Assignee: Aventis, Pharma S.A., Antony (FR)

( * ) Notice: Subject to any disclaimer, the term of this patent is extended or adjusted under 35 U.S.C. 154(b) by 0 days.

(21) Appl. No.: 10/622,655

(22) Filed: Jul. 18, 2003

(65) Prior Publication Data

US 2004/0058919 A1 Mar. 25, 2004

(30) Foreign Application Priority Data

Jul. 23, 2002 (FR) .............................. 02 09334

(51) Int. Cl.$^7$ ...................... A61K 31/47; C07D 215/04
(52) U.S. Cl. ..................... 514/314; 514/311; 546/174; 546/177; 546/178; 546/179; 546/180
(58) Field of Search ................. 514/314, 311; 546/174, 177, 178, 179, 180

(56) References Cited

U.S. PATENT DOCUMENTS

| | | | |
|---|---|---|---|
| 4,670,446 A | * | 6/1987 | Mestre et al. ............... 514/314 |
| 6,403,610 B1 | | 6/2002 | Malleron et al. |
| 6,602,884 B2 | * | 8/2003 | Bacque et al. .............. 514/314 |
| 2002/0111492 A1 | | 8/2002 | Baque et al. |

FOREIGN PATENT DOCUMENTS

| | | |
|---|---|---|
| EP | 0 030 044 | 6/1981 |
| FR | 2 354 771 | 1/1978 |
| WO | WO 99/37635 | 7/1999 |
| WO | WO 00/43383 | 7/2000 |
| WO | WO 01/25227 | 4/2001 |
| WO | WO 02/40474 | 5/2002 |

* cited by examiner

Primary Examiner—D. Margaret Seaman
(74) Attorney, Agent, or Firm—Irving Newman

(57) ABSTRACT

Quinolylpropylpiperidine derivatives of general formula (I) in which:

$R_1$ is $NH_2$, alkylamino, dialkylamino, hydroxyamino, alkyl(alkyloxy)amino or alkyloxyamino, $R_2$ is a carboxyl, carboxymethyl or hydroxymethyl radical, $R_3$ is alkyl (1 to 6C) substituted by phenylthio which can itself carry 1 to 3 substituents selected from halogen, OH, alkyl, alkyloxy, $CF_3$, $OCF_3$, COOH, alkyloxycarbonyl, CN and $NH_2$, by cycloalkylthio (3 to 7 members) or by heteroarylthio (5 to 6 members) comprising 1 to 4 heteroatoms selected from N, S and O and optionally itself substituted [by halogen, OH, alkyl, alkyloxy, $CF_3$, $OCF_3$, =O, COOH, alkyloxycarbonyl, CN or $NH_2$] or $R_3$ is propargyl substituted by phenyl which can itself carry 1 to 3 substituents selected from halogen, OH, alkyl, alkyloxy, $CF_3$, $OCF_3$, COOH, alkyloxycarbonyl, CN and $NH_2$ or substituted by cycloalkyl comprising 3 to 7 members or substituted by 5- to 6-membered heteroaryl comprising 1 to 4 heteroatoms chosen from N, O or S and optionally itself substituted by halogen, OH, alkyl, alkyloxy, $CF_3$, $OCF_3$, =O, COOH, alkyloxycarbonyl, CN or $NH_2$, and $R_4$ is alkyl (1 to 6C), alkenyl-$CH_2$—, alkynyl-$CH_2$— (3 to 7C), cycloalkyl or (cycloalkyl)alkyl, in their diastereoisomeric forms or their mixtures, and their pharmaceutically acceptable salts.

These novel derivatives are particularly advantageous antimicrobial agents.

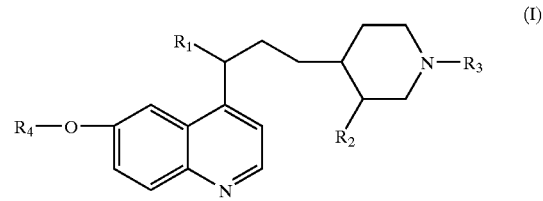

(I)

8 Claims, No Drawings

QUINOLYLPROPYLPIPERIDINE DERIVATIVES, PREPARATION PROCESS AND INTERMEDIATES, AND COMPOSITIONS INCLUDING THEM

CROSS-REFERENCE

This application claims priority from French Patent Application No. 0209334, filed Jul. 23, 2002.

SUMMARY OF THE INVENTION

The present invention relates to quinolylpropylpiperidine derivatives of general formula:

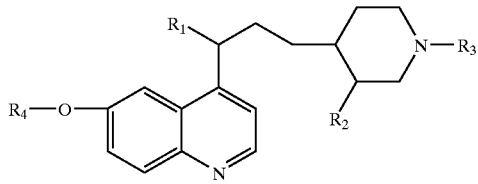

which are particularly active as antimicrobial agents. The invention also relates to their preparation and to the compositions comprising them.

BACKGROUND OF THE INVENTION

Patent applications WO 99/37635 and WO 00/43383 have disclosed antimicrobial quinolylpropylpiperidine derivatives of general formula:

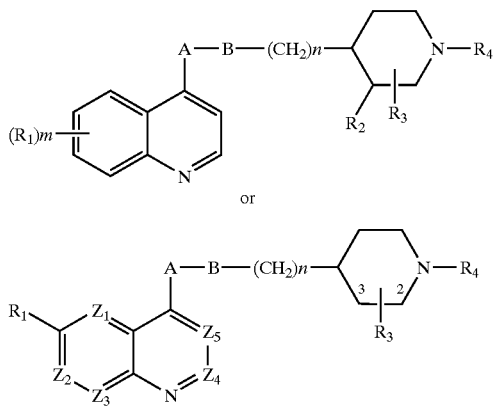

in which the $R_1$ radical is, in particular, $(C_{1-6})$alkoxy, $R_2$ is hydrogen, $R_3$ is in the 2- or 3-position and represents $(C_{1-6})$alkyl which can optionally be substituted by 1 to 3 substituents chosen from thiol, halogen, alkylthio, trifluoromethyl, carboxyl, alkyloxycarbonyl, alkylcarbonyl, alkenyloxycarbonyl, alkenylcarbonyl, hydroxyl optionally substituted by alkyl, and the like, $R_4$ is a —$CH_2$—$R_5$ group in which $R_5$ is selected from alkyl, hydroxyalkyl, alkenyl, alkynyl, tetrahydrofuryl, optionally substituted phenylalkyl, optionally substituted phenylalkenyl, optionally substituted heteroarylalkyl, optionally substituted heteroaroyl, and the like, n is 0 to 2, m is 1 or 2 and A and B are in particular oxygen, sulfur, sulfinyl, sulfonyl, $NR_{11}$, $R_{11}$ being selected from H, CF3, alkyl, alkenyl, alkoxycarbonyl, alkylcarbonyl and, possibly substituted aminocarbonyl, or $CR_6R_7$, in which $R_6$ and $R_7$ represent H, thiol, alkylthio, halo, trifluoromethyl, alkenyl, alkenylcarbonyl, hydroxyl or amino, and $Z_1$ to $Z_5$ are N or $CR_{1a}$ wherein $R_{1a}$ is H or $R_1$, and the like.

European patent application EP 30 044 has disclosed quinoline derivatives, of use as cardiovasculars, corresponding to the general formula:

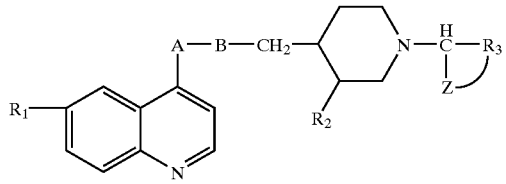

in which A-B is —$CH_2$—$CH_2$—, —CHOH—$CH_2$—, —$CH_2$—CHOH—, —$CH_2$—CO— or —CO—$CH_2$—, $R_1$ is H, OH or alkyloxy, $R_2$ is ethyl or vinyl, $R_3$ is, in particular, alkyl, hydroxyalkyl, cycloalkyl, hydroxyl, alkenyl, alkynyl, tetrahydrofuryl, phenylalkyl, optionally substituted diphenylalkyl, optionally substituted phenylalkenyl, optionally substituted benzoyl, optionally substituted benzoylalkyl, optionally substituted heteroaryl or optionally substituted heteroarylalkyl, and Z is H or alkyl or, alternatively, together with $R_3$, forms a cycloalkyl radical.

DETAILED DESCRIPTION

It has now been found, and it is this which forms the subject matter of the present invention, that the products of general formula (I) in which:

$R_1$ is an amino, alkylamino, dialkylamino, hydroxyamino, alkyloxyamino, or alkyl(alkyloxy)amino radical, $R_2$ is a carboxyl, carboxymethyl or hydroxymethyl radical, $R_3$ is an alkyl radical having 1 to 6 carbon atoms substituted by a substituent selected from a.) a phenylthio radical which, itself, has 1 to 4 substituents selected from halogen, hydroxyl, alkyl, alkyloxy, trifluoromethyl, trifluoromethoxy, carboxyl, alkyloxycarbonyl, cyano and amino, b.) a cycloalkylthio radical, the cyclic part of which comprises 3 to 7 members, or c.) a 5- to 6-membered heteroarylthio radical comprising 1 to 4 heteroatoms selected from nitrogen, oxygen and sulfur and optionally substituted by a one or more substituents selected from halogen, hydroxyl, alkyl, alkyloxy, trifluoromethyl, trifluoromethoxy, oxo, carboxyl, alkyloxycarbonyl, cyano and amino; or, alternatively, $R_3$ is a propargyl radical that is (a) substituted by a phenyl radical which can, in turn, be substituted by 1 to 4 substituents selected from halogen, hydroxyl, alkyl, alkyloxy, trifluoromethyl, trifluoromethoxy, carboxyl, alkyloxycarbonyl, cyano and amino or (b) substituted by a cycloalkyl radical comprising 3 to 7 members or (c) substituted by a 5- to 6-membered heteroaryl radical comprising 1 to 4 heteroatoms selected from nitrogen, oxygen and sulfur, said heteroaryl radical being optionally itself substituted by one or more substituents selected from halogen, hydroxyl, alkyl, alkyloxy, trifluoromethyl, trifluoromethoxy, oxo, carboxyl, alkyloxycarbonyl, cyano and amino, and $R_4$ represents an alkyl radical comprising 1 to 6 carbon atoms, an alkenyl-$CH_2$— radical, the alkenyl portion of which comprises 2 to 6 carbon atoms, an alkynyl-$CH_2$— radical, the alkynyl portion of which comprises 2 to 6 carbon atoms, a cycloalkyl radical the cyclic part of which comprises 3 to 8 atoms, or a (cycloalkyl)alkyl radical, the cyclic part of which comprises 3 to 8 atoms, in their diastereoisomeric forms or their mixtures and/or in their cis or trans forms, and their salts, are powerful antibacterial agents.

It is understood that, in the above general formula, the alkyl radicals and portions are straight-chain or branched-chain radicals and portions and comprise, except when otherwise specifically mentioned, 1 to 4 carbon atoms.

In the above general formula, when $R_3$ carries a heteroaryl substituent, the latter can be chosen (without implied limitation) from thienyl, furyl, pyrrolyl, imidazolyl, thiazolyl, oxazolyl, thiadiazolyl, oxadiazolyl, tetrazolyl, pyridyl, pyridazinyl, pyrazinyl or pyrimidinyl. It is also understood that, in the definition of $R_3$, the substituted alkyl radical carries only a single cyclic substituent.

According to the invention, the products of general formula (I) can be obtained by condensation of the $R_3$ chain onto the quinolylpropylpiperidine derivative of general formula:

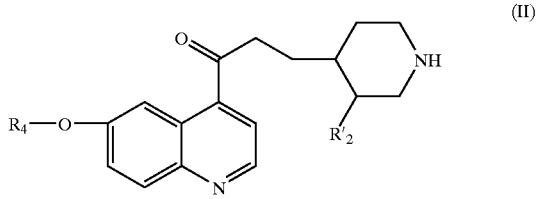

(II)

in which $R_4$ is defined as above and $R'_2$ represents a protected carboxyl radical or a protected carboxymethyl radical, in order to obtain a quinolylpropylpiperidine derivative of general formula:

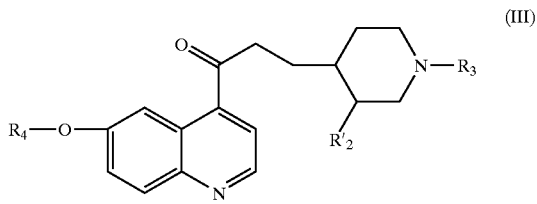

(III)

in which $R'_2$, $R_4$ and $R_3$ are defined as above, followed by the conversion of the oxo radical to a hydroxyimino or alkyloxyimino radical, in order to obtain a quinolylpropylpiperidine derivative of general formula:

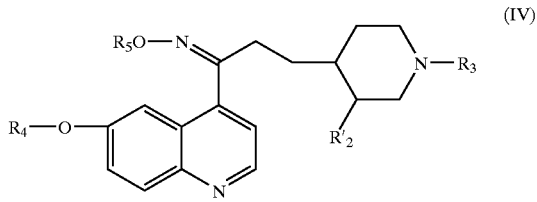

(IV)

in which $R'_2$, $R_3$ and $R_4$ are defined as above and $R_5$ is a hydrogen atom or an alkyl radical, then, if appropriate, followed by the reduction of the derivative of general formula (IV) in which $R_5$ is a hydrogen atom to an amine and optionally by the conversion to a monoalkylated or dialkylated amine, or followed by the reduction of the derivative of general formula (IV) in which $R_5$ is a hydrogen atom to a hydroxylamine or in which $R_5$ is alkyl to an alkyloxyamine, then, if appropriate, followed by the conversion of the derivative obtained in which $R_1$ is alkyloxyamino to alkyl(alkyloxy)amino by alkylation, then followed by the conversion of $R'_2$ to a carboxyl or carboxymethyl radical, and/or, if appropriate, followed by the reduction of the carboxyl radical thus obtained or of the protected carboxyl radical which $R'_2$ can represent to a hydroxymethyl radical and, optionally, by the conversion of the latter to a carboxymethyl radical according to the usual methods, and, optionally, by the conversion of the product obtained to a salt.

The condensation of the $R_3$ chain onto the piperidine is advantageously carried out by the action of a derivative of general formula:

$$R_3\text{—}X \qquad (V)$$

in which $R_3$ is defined as above and X represents a halogen atom, a methylsulfonyloxy radical, a trifluoromethylsulfonyloxy radical or a p-toluenesulfonyloxy radical, the reaction being carried out in an anhydrous environment, preferably an inert environment (nitrogen or argon, for example), in an organic solvent, such as an amide (dimethylformamide, for example), a ketone (acetone, for example) or a nitrile (acetonitrile, for example), in the presence of a base, such as a nitrogenous organic base (for example, triethylamine) or an inorganic base (alkaline carbonate: potassium carbonate, for example), at a temperature of between 20° C. and the reflux temperature of the solvent. The reaction can optionally be carried out in the presence of an alkaline iodide (sodium iodide or potassium iodide, for example). Preferably, the reaction is carried out with a derivative in which X is a bromine or iodine atom.

When $R_3$ represents propargyl substituted by phenyl, cycloalkyl or heterocyclyl, it can also be preferable to condense a propargyl halide and then to substitute the chain with a phenyl, cycloalkyl or heterocyclyl radical. In this alternative, the addition of the propargyl chain is carried out by means of propargyl bromide under the conditions set out above for $R_3$, in the presence or absence of an alkali metal iodide, such as, for example, potassium iodide or sodium iodide.

When it is a matter of the substitution by a phenyl or heterocyclyl radical, the reaction is carried out by the action of a halide derived from the cyclic radical to be substituted, in the presence of triethylamine, in an anhydrous medium, optionally without solvent or in a solvent, such as an amide (dimethylformamide, for example) or a nitrile (acetonitrile, for example), and in the presence of a palladium salt, such as, for example, tetrakis(triphenylphosphine)palladium, and of cuprous iodide, at a temperature of between 20° C. and the reflux temperature of the solvent.

When it is a matter of the substitution by a cycloalkyl group, the reaction is carried out by the action of an organolithium compound, such as n-butyllithium or tert-butyllithium, on the propargyl derivative obtained above, in an anhydrous medium in an ether, such as, for example, tetrahydrofuran, at a temperature of between about −78 and 0° C., and then the action of a cycloalkanone, followed by the deoxygenation of the intermediate alcohol according to conventional methods.

It is understood that, when the alkyl radicals represented by $R_3$ carry carboxyl or amino substituents, the latter are protected beforehand and then deprotected after the reaction. These operations are carried out according to the usual methods which do not detrimentally affect the remainder of the molecule, in particular according to the methods described by T. W. Greene and P. G. M. Wuts, Protective Groups in Organic Synthesis (2nd ed.), A. Wiley—Interscience Publication (1991), or by McOmie, Protective Groups in Organic Chemistry, Plenum Press (1973).

The protected carboxyl radical represented by R'$_2$ can be chosen from easily hydrolyzable esters. Mention may be made, by way of example, of methyl, benzyl or tert-butyl esters or, alternatively, allyl or phenylpropyl esters. The protecting of the carboxyl radical is optionally carried out simultaneously with the reaction. In this case, the product of general formula (II) employed carries, as an R'$_2$ radical, a carboxyl radical.

The conversion of the oxo radical to a hydroxyimino or alkyloxyimino radical is carried out by the action of hydroxylamine (hydroxylamine hydrochloride, for example) or of alkyloxyamine, optionally in the hydrochloride form, in a solvent, such as pyridine or an alcohol (such as methanol or ethanol, for example), and in the presence of a nitrogenous base, such as triethylamine or pyridine, at a temperature of between about 0 and 60° C.

The reduction to amine is carried out according to the usual methods which do not detrimentally affect the remainder of the molecule, in particular, by the action of a reducing agent, such as, for example, a hydride (alkaline borohydride: sodium borohydride or potassium borohydride, for example, or lithium aluminum hydride), in the presence or absence of molybdenum oxide, the reduction preferably being carried out under an inert atmosphere (nitrogen or argon, for example) in an organic solvent, such as an alcohol (methanol, ethanol or isopropanol, for example) or a chlorinated solvent (for example dichloromethane), at a temperature of between about −10 and 40° C.

The reduction to hydroxylamine or to alkyloxyamine is carried out in particular in the presence of an organic acid (carboxylic acid, such as, for example, acetic acid) by the action of a reducing agent, such as, for example, a hydride chosen from sodium triacetoxyborohydride (optionally prepared in situ) or sodium cyanoborohydride, preferably under an inert atmosphere (nitrogen or argon, for example), in an organic solvent, such as an alcohol (methanol, ethanol or isopropanol, for example) or a chlorinated solvent (for example dichloromethane), at a temperature of between about −30 and +40° C.

The conversion of the amino radical represented by R$_1$ to an alkylamino or dialkylamino radical is carried out according to the usual methods, in particular by the action of an alkyl halide, optionally in a basic medium in the presence of a nitrogenous base, such as a trialkylamine (triethylamine, diisopropylethylamine, and the like) or pyridine, or in the presence of an alkali metal hydride (sodium hydride), in an inert solvent, such as an amide (dimethylformamide, for example) or an oxide (dimethyl sulfoxide, for example), at a temperature of between about 20° C. and the reflux temperature of the reaction mixture.

The conversion of the alkyloxyamino radical represented by R$_1$ to an alkyl(alkyloxy)amino radical is carried out according to the method described above for the alkylation of the amine.

The reduction of the acid, protected in the form of an R'$_2$ radical, in the 3-position of the piperidine to a hydroxymethyl radical is carried out according to the usual methods known to a person skilled in the art which do not detrimentally affect the remainder of the molecule; in particular, the reduction is carried out by the action of a hydride (lithium aluminum hydride or diisobutylaluminum hydride, for example) in a solvent, such as an ether (tetrahydrofuran, for example), at a temperature of between about 20 and 60° C.

The reduction of the free acid can be carried out according to methods also known to a person skilled in the art, for example by hydrogenation in the presence of a rhodium- or ruthenium-based catalyst, by the action of sodium borohydride in the presence of Lewis acids or by the action of lithium aluminum hydride in ether.

The conversion of the hydroxymethyl radical in the 3-position of the piperidine to a carboxymethyl radical is carried out according to the usual methods which do not detrimentally affect the remainder of the molecule; in particular, it can be carried out by the action of a halogenating agent, such as, for example, thionyl chloride or phosphorus trichloride or phosphorus tribromide, and then of an alkaline cyanide (potassium cyanide or sodium cyanide, for example), in order to prepare the corresponding cyanomethyl derivative, followed by the hydrolysis of the nitrile. When the R$_1$ radical is an amino radical, it is preferable to protect this radical beforehand according to the known methods cited above for R$_3$. The halogenation can be carried out in a chlorinated solvent (dichloromethane or chloroform, for example) at a temperature of between about 0° C. and the reflux temperature of the solvent.

The reaction of the alkaline cyanide can be carried out in a solvent, such as dimethyl sulfoxide, an amide (dimethylformamide, for example), a ketone (acetone, for example), an ether, such as, for example, tetrahydrofuran, or an alcohol, such as, for example, methanol or ethanol, at a temperature of between about 20° C. and the reflux temperature of the reaction mixture.

The hydrolysis of the nitrile is carried out according to conventional methods which do not detrimentally affect the remainder of the molecule, in particular by the action of hydrochloric acid in a methanolic medium, at a temperature of between about 20 and 70° C., followed by the saponification of the ester obtained (for example, by sodium hydroxide in a mixture of dioxane and water), or else directly by the action of aqueous sulfuric acid at a temperature of between about 50 and 80° C.

The removal, if appropriate, of the acid-protecting radical, in order to obtain a quinolylpropylpiperidine derivative in which R$_2$ is a carboxyl radical, is carried out according to the usual methods, in particular by acid hydrolysis or saponification of the R'$_2$ ester. In particular, sodium hydroxide is reacted in an aqueous/organic medium, for example in an alcohol, such as methanol, or an ether, such as dioxane, at a temperature of between about 20° C. and the reflux temperature of the reaction mixture. The hydrolysis can also be carried out in an aqueous hydrochloric acid medium at a temperature of between about 20 and 100° C.

The quinolylpropylpiperidine derivative of general formula (II) or the corresponding acid in which R'$_2$ represents a carboxyl radical can be prepared according to or by analogy with the methods described hereinafter in the examples or according to or by analogy with the methods disclosed in European patent application EP 30 044 or in international application WO 99/37635. The intermediates of the quinolylpropylpiperidine derivatives in which R$_4$ represents alkenyl-CH$_2$—, alkynyl-CH$_2$—, cycloalkyl or (cycloalkyl)alkyl can be obtained, by analogy with the preparation of the intermediates in which R$_4$ is alkyl, by the action of the corresponding halogenated derivative on the quinoline derivative hydroxylated in the 6-position.

It is understood that the derivatives of general formula (I), (II), (III) or (IV) or their starting intermediates can exist in the cis or trans form with regard to the substituents in the 3- and 4-positions of the piperidine. The derivatives with the trans configuration can be obtained from the derivatives with the cis configuration according to or by analogy with the method disclosed in international application WO 99/37635.

The quinolylpropylpiperidine derivatives of general formula (I) can be purified, if appropriate, by physical methods, such as crystallization or chromatography.

Furthermore, it is understood that, when $R_1$ is optionally substituted amino, diastereoisomeric forms exist and that the diastereoisomeric forms and their mixtures also come within the scope of the present invention. The latter can be separated in particular by silica gel chromatography or by High Performance Liquid Chromatography (HPLC).

The quinolylpropylpiperidine derivatives of general formula (I) can be converted to addition salts with acids by known methods. It is understood that these salts also come within the scope of the present invention.

Mention may be made, as examples of addition salts with pharmaceutically acceptable acids, of the salts formed with inorganic acids (hydrochlorides, hydrobromides, sulfates, nitrates or phosphates) or with organic acids (succinates, fumarates, tartrates, acetates, propionates, maleates, citrates, methanesulfonates, ethanesulfonates, phenylsulfonates, p-toluenesulfonates, isethionates, naphthylsulfonates or camphorsulfonates) or with substituted derivatives of these compounds.

Some of the quinolylpropylpiperidine derivatives of general formula (I) carrying a carboxyl radical can be converted to the form of metal salts or to addition salts with nitrogenous bases according to methods known per se. These salts also come within the scope of the present invention. The salts can be obtained by the action of a metal base (for example, an alkali metal or alkaline earth metal base), of ammonia or of an amine on a product according to the invention in an appropriate solvent, such as an alcohol, an ether or water, or by an exchange reaction with a salt of an organic acid. The salt formed precipitates, after optional concentration of the solution, and is separated by filtration, settling or lyophilization. Mention may be made, as examples of pharmaceutically acceptable salts, of the salts with alkali metals (sodium, potassium or lithium) or with alkaline earth metals (magnesium or calcium), the ammonium salt or the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine or dibenzylamine).

The quinolylpropylpiperidine derivatives of general formula (IV) are novel derivatives which are of use in particular as intermediates in the preparation of the products according to the invention.

The quinolylpropylpiperidine derivatives obtained during the implementation of the process according to the invention before the removal of the group protecting the carboxyl radical and the optional conversion of the latter or of its protected form to a hydroxymethyl radical, that is to say the derivatives of general formula (VI)

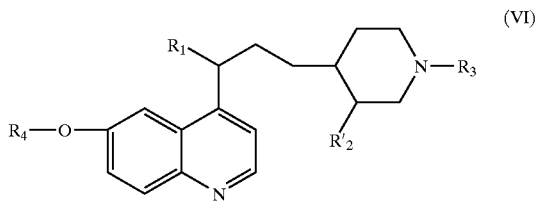

(VI)

in which $R_1$, $R'_2$, $R_3$ and $R_4$ are defined as above, are also novel derivatives.

The quinolylpropylpiperidine derivatives according to the invention are particularly advantageous antibacterial agents, in particular because of their activity with regard to *Haemophilus influenzae*.

In vitro, with regard to gram-positive microorganisms, the quinolylpropylpiperidine derivative illustrated in the example hereinafter has proved to be active at a concentration of 2 μg/ml with regard to meticillin-resistant *Staphylococcus aureus* AS5155, at a concentration of 1 μg/ml with regard to *Streptococcus pneumoniae* 6254-01 and at a concentration of 8 μg/ml with regard to *Enterococcus faecium* ATCC29212 or H983401 and, with regard to gram-negative microorganisms, it has proved to be active at a concentration of 0.12 μg/ml with regard to *Moraxella catharrhalis* IPA152 and at a concentration of 2 mg/l with regard to *Haemophilus influenzae* Barbier; in vivo, it has proved to be active with regard to experimental infections of mice with *Staphylococcus aureus* IP8203 at a dose of 65 mg/kg subcutaneously ($DC_{50}$) and at a dose of 70 mg/kg orally ($DC_{50}$).

Finally, the products according to the invention are in particular advantageous because of their low toxicity. The product of the example illustrated hereinafter did not display any toxicity at a dose of 100 mg/kg subcutaneously in mice (2 administrations).

Among the products according to the invention, the quinolylpropylpiperidine derivatives listed hereinbelow or described hereinafter in the experimental part are more particularly advantageous:

(3R,4R)-4-[3-(R,S)-Amino-3-(6-methoxyquinolin-4-yl)propyl]-1-[2-(2,5-difluoro-phenylthio)ethyl]piperidine-3-carboxylic acid (3R,4R)-4-[3-(R,S)-Amino-3-(6-methoxyquinolin-4-yl)propyl]-1-[2-(3,5-diflouro-phenylthio)ethyl]piperidine-3-carboxylic acid (3R,4R)-4-[3-(R,S)-Amino-3-(6-methoxyquinolin-4-yl)propyl]-1-[2-(cyclopentylthio)-ethyl]piperidine-3-carboxylic acid (3R,4R)-4-[3-(R,S)-Amino-3-(6-methoxyquinolin-4-yl)propyl]-1-[2-(cyclohexylthio)-ethyl]piperidine-3-carboxylic acid (3R,4R)-4-[3-(R,S)-Amino-3-(6-methoxyquinolin-4-yl)propyl]-1-[2-(1,3-thiazol-2-yl)-thioethyl]piperidine-3-carboxylic acid (3R,4R)-4-[3-(R,S)-Amino-3-(6-methoxyquinolin-4-yl)propyl]-1-[2-(pyridin-2-yl)-thioethyl]piperidine-3-carboxylic acid (3R,4R)-4-[3-(R,S)-Amino-3-(6-methoxyquinolin-4-yl)propyl]-1-[3-(3,5-difluoro-phenyl)prop-2-ynyl]piperidine-3-carboxylic acid (3R,4R)-4-[3-(R,S)-Amino-3-(6-methoxyquinolin-4-yl)propyl]-1-[3-(thien-2-yl)prop-2-ynyl]piperidine-3-carboxylic acid (3R,4R)-4-[3-(R,S)-Methylamino-3-(6-methoxyquinolin-4-yl)propyl]-1-[2-(2,5-difluoro-phenylthio)ethyl]piperidine-3-carboxylic acid (3R,4R)-4-[3-(R,S)-Methylamino-3-(6-methoxyquinolin-4-yl)propyl]-1-[2-(3,5-difluoro-phenylthio)ethyl]piperidine-3-carboxylic acid (3R,4R)-4-[3-(R,S)-Methylamino-3-(6-methoxyquinolin-4-yl)propyl]-1-[2-(cyclopentyl-thio)ethyl]piperidine-3-carboxylic acid (3R,4R)-4-[3-(R,S)-Methylamino-3-(6-methoxyquinolin-4-yl)propyl]-1-[2-(cyclohexyl-thio)ethyl]piperidine-3-carboxylic acid (3R,4R)-4-[3-(R,S)-Methylamino-3-(6-methoxyquinolin-4-yl)propyl]-1-[2-(thien-2yl)-thioethyl]piperidine-3-carboxylic acid (3R,4R)-4-[3-(R,S)-Methylamino-3-(6-methoxyquinolin-4-yl)propyl]-1-[2-(1,3-thiazol-2-yl)thioethyl]piperidine-3-carboxylic acid (3R,4R)-4-[3-(R,S)-Methylamino-3-(6-methoxyquinolin-4-yl)propyl]-1-[2-(pyridin-2-yl)thioethyl]piperidine-3-carboxylic acid (3R,4R)-4-[3-(R,S)-Methylamino-3-(6-methoxyquinolin-4-yl)propyl]-1-[3-(3,5-difluoro-phenyl)prop-2-ynyl]piperidine-3-carboxylic acid (3R,4R)-4-[3-(R,S)-Methylamino-3-(6-methoxyquinolin-4-yl)propyl]-1-[3-(2,3,5-tri-fluorophenyl)prop-2-ynyl]piperidine-3-carboxylic acid (3R,4R)-4-[3-(R,S)-Methylamino-3-(6-methoxyquinolin-4-yl)propyl]-1-[3-(thien-2-yl)-prop-2-ynyl]piperidine-3-carboxylic acid (3R,4R)-4-[3-(R,S)-Dimethylamino-3-(6-methoxyquinolin-4-yl)propyl]-1-[2-(2,5-difluorophenylthio)ethyl]piperidine-3-carboxylic acid (3R,4R)-4-[3-(R,S)-Dimethylamino-3-(6-methoxyquinolin-4-yl)propyl]-1-[2-(3,5-difluorophenylthio)ethyl]piperidine-3-carboxylic acid (3R,4R)-4-[3-(R,S)-Dimethylamino-3-(6-methoxyquinolin-4-yl)propyl]-1-[2-(cyclo-pentylthio)ethyl]piperidine-3-carboxylic acid (3R,4R)-4-[3-(R,S)-Dimethylamino-3-(6-methoxyquinolin-4-yl)propyl]-1-[2-(cyclo-hexylthio)ethyl]piperidine-3-carboxylic acid (3R,4R)-4-[3-(R,S)-Dimethylamino-3-(6-methoxyquinolin-4-yl)propyl]-1-[2-(thien-2-yl)thioethyl]piperidine-3-carboxylic acid (3R,4R)-4-[3-(R,S)-Dimethylamino-3-(6-methoxyquinolin-4-yl)propyl]-1-[2-(1,3-thiazol-2-yl)thioethyl]piperidine-3-carboxylic acid (3R,4R)-4-[3-(R,S)-Dimethylamino-3-(6-methoxyquinolin-4-yl)propyl]-1-[2-(pyridin-2-yl)thioethyl]piperidine-3-carboxylic acid (3R,4R)-4-[3-(R,S)-Dimethylamino-3-(6-methoxyquinolin-4-yl)propyl]-1-[3-(3,5-difluorophenyl)prop-2-ynyl]piperidine-3-carboxylic acid (3R,4R)-4-[3-(R,S)-Dimethylamino-3-(6-methoxyquinolin-4-yl)propyl]-1-[3-(2,3-trifluorophenylthio)prop-2-ynyl]piperidine-3-carboxylic acid (3R,4R)-4-[3-(R,S)-Dimethylamino-3-(6-methoxyquinolin-4-yl)propyl]-1-[3-(thien-2-yl)prop-2-ynyl]piperidine-3-carboxylic acid (3R,4R)-4-[3-(R,S)-Hydroxyamino-3-(6-methoxyquinolin-4-yl)propyl]-1-[2-(2,5-difluorophenylthio)ethyl]piperidine-3-carboxylic acid (3R,4R)-4-[3-(R,S)-Hydroxyamino-3-(6-methoxyquinolin-4-yl)propyl]-1-[2-(3,5-difluorophenylthio)ethyl]piperidine-3-carboxylic acid (3R,4R)-4-[3-(R,S)-Hydroxyamino-3-(6-methoxyquinolin-4-yl)propyl]-1-[2-(cyclo-phenylthio)ethyl]piperidine-3-carboxylic acid (3R,4R)-4-[3-(R,S)-Hydroxyamino-3-(6-methoxyquinolin-4-yl)propyl]-1-[2-(cyclo-hexylthio)ethyl]piperidine-3-carboxylic acid (3R,4R)-4-[3-(R,S)-Hydroxyamino-3-(6-methoxyquinolin-4-yl)propyl]-1-[2-(thien-2-yl)thioethyl]piperidine-3-carboxylic acid (3R,4R)-4-[3-(R,S)-Hydroxyamino-3-(6-methoxyquinolin-4-yl)propyl]-1-[2-(1,3-thiazol-2-yl)thioethyl]piperidine-3-carboxylic acid (3R,4R)-4-[3-(R,S)-Hydroxyamino-3-(6-methoxyquinolin-4-yl)propyl]-1-[2-(pyridin-2-yl)thioethyl]piperidine-3-carboxylic acid (3R,4R)-4-[3-(R,S)-Hydroxyamino-3-(6-methoxyquinolin-4-yl)propyl]-1-[3-(3,5-difluorophenylthio)prop-2-ynyl]piperidine-3-carboxylic acid (3R,4R)-4-[3-(R,S)-Hydroxyamino-3-(6-methoxyquinolin-4-yl)propyl]-1-[3-(2,3,5-trifluorophenylthio)prop-2-ynyl]piperidine-3-carboxylic acid (3R,4R)-4-[3-(R,S)-Hydroxyamino-3-(6-methoxyquinolin-4-yl)propyl]-1-[3-(thien-2-yl)prop-2-ynyl]piperidine-3-carboxylic acid (3R,4R)-4-[3-(R,S)-Methoxyamino-3-(6-methoxyquinolin-4-yl)propyl]-1-[2-(2,5-fluorophenylthio)ethyl]piperidine-3-carboxylic acid (3R,4R)-4-[3-(R,S)-Methoxyamino-3-(6-methoxyquinolin-4-yl)propyl]-1-[2-(3,5-difluorophenylthio)ethyl]piperidine-3-carboxylic acid (3R,4R)-4-[3-(R,S)-Methoxyamino-3-(6-methoxyquinolin-4-yl)propyl]-1-[2-(cyclo-phenylthio)ethyl]piperidine-3-carboxylic acid (3R,4R)-4-[3-(R,S)-Methoxyamino-3-(6-methoxyquinolin-4-yl)propyl]-1-[2-(cyclo-hexylthio)ethyl]piperidine-3-carboxylic acid (3R,4R)-4-[3-(R,S)-Methoxyamino-3-(6-methoxyquinolin-4-yl)propyl]-1-[2-(thien-2-yl)thioethyl]piperidine-3-carboxylic acid (3R,4R)-4-[3-(R,S)-Methoxyamino-3-(6-methoxyquinolin-4-yl)propyl]-1-[2-(1,3-thiazol-2-yl)thioethyl]piperidine-3-carboxylic acid (3R,4R)-4-[3-(R,S)-Methoxyamino-3-(6-methoxyquinolin-4-yl)propyl]-1-[2-(pyridin-2-yl)thioethyl]piperidine-3-carboxylic acid (3R,4R)-4-[3-(R,S)-Methoxyamino-3-(6-methoxyquinolin-4-yl)propyl]-1-[3-(3,5difluorophenyl)prop-2-ynyl]piperidine-3-carboxylic acid (3R,4R)-4-[3-(R,S)-Methoxyamino-3-(6-methoxyquinolin-4-yl)propyl]-1-[3-(2,3,5-trifluorophenyl)prop-2-ynyl]piperidine-3-carboxylic acid (3R,4R)-4-[3-(R,S)-Methoxyamino-3-(6-methoxyquinolin-4-yl)propyl]-1-[3-(thien-2-yl)prop-2-ynyl]piperidine-3-carboxylic acid (3R,4R)-4-[3-(R,S)-Amino-3-(6-methoxyquinolin-4-yl)propyl]-1-[2-(2,5-difluoro-phenylthio)ethyl]piperidine-3-acetic acid (3R,4R)-4-[3-(R,S)-Amino-3-(6-methoxyquinolin-4-yl)propyl]-1-[2-(3,5-difluoro-phenylthio)ethyl]piperidine-3-acetic acid (3R,4R)-4-[3-(R,S)-Amino-3-(6-methoxyquinolin-4-yl)propyl]-1-[2-(cyclopentylthio)-ethyl]piperidine-3-acetic acid (3R,4R)-4-[3-(R,S)-Amino-3-(6-methoxyquinolin-4-yl)propyl]-1-[2-(cyclohexylthio)-ethyl]piperidine-3-acetic acid (3R,4R)-4-[3-(R,S)-Amino-3-(6-methoxyquinolin-4-yl)propyl]-1-[2-(thien-2-yl)thio-ethyl]piperidine-3-acetic acid (3R,4R)-4-[3-(R,S)-Amino-3-(6-methoxyquinolin-4-yl)propyl]-1-[2-(1,3-thiazol-2yl)-thioethyl]piperidine-3-acetic acid (3R,4R)-4-[3-(R,S)-Amino-3-(6-methoxyquinolin-4-yl)propyl]-1-[2-(pyridin-2-yl)thio-ethyl]piperidine-3-acetic acid (3R,4R)-4-[3-(R,S)-Amino-3-(6-methoxyquinolin-4-yl)propyl]-1-[3-(3,5-difluorophenyl)prop-2-ynyl]piperidine-3-acetic acid (3R,4R)-4-[3-(R,S)-Amino-3-(6-methoxyquinolin-4-yl) propyl]-1-[3-(2,3,5-trifluorophenyl)prop-2-ynyl] piperidine-3-acetic acid (3R,4R)-4-[3-(R,S)-Amino-3-(6-methoxyquinolin-4-yl) propyl]-1-[3-(thien-2-yl)-prop-2-ynyl]piperidine-3-acetic acid (3R,4R)-4-[3-(R,S)-Methylamino-3-(6-methoxyquinolin-4-yl)propyl]-1-[2-(2,5-di-difluorophenyl)ethyl]piperidine-3-acetic acid (3R,4R)-4-[3-(R,S)-Methylamino-3-(6-methoxyquinolin-4-yl)propyl]-1-[2-(3,5-di-difluorophenylthio)ethyl]piperidine-3-acetic acid (3R,4R)-4-[3-(R,S)-Methylamino-3-(6-methoxyquinolin-4-yl)propyl]-1-[2-(cyclopentyl-thio)ethyl]piperidine-3-acetic acid (3R,4R)-4-[3-(R,S)-Methylamino-3-(6-methoxyquinolin-4-yl)propyl]-1-[2-(cyclo-hexylthio)ethyl]piperidine-3-acetic acid (3R,4R)-4-[3-(R,S)-Methylamino-3-(6-methoxyquinolin-4-yl)propyl]-1-[2-(thien-2-yl)-thioethyl]piperidine-3-acetic acid (3R,4R)-4-[3-(R,S)-Methylamino-3-(6-methoxyquinolin-4-yl)propyl]-1-[2-(1,3-thiazol-2-yl)thioethyl]piperidine-3-acetic acid (3R,4R)-4-[3-(R,S)-Methylamino-3-(6-methoxyquinolin-4-yl)propyl]-1-[2-(pyridin-2-yl)thioethyl]piperidine-3-acetic acid (3R,4R)-4-[3-(R,S)-Methylamino-3-(6-methoxyquinolin-4-yl)propyl]-1-[3-(3,5-difluoro-phenyl)prop-2-ynyl]piperidine-3-acetic acid (3R,4R)-4-[3-(R,S)-Methylamino-3-(6-methoxyquinolin-4-yl)propyl]-1-[3-(2,3,5-tri-fluorophenyl)prop-2-ynyl]piperidine-3-acetic acid (3R,4R)-4-[3-(R,S)-Methylamino-3-(6-methoxyquinolin-4-yl)propyl]-1-[3-(thien-2yl)prop-2-ynyl]piperidine-3-acetic acid (3R,4R)-4-[3-(R,S)-Dimethylamino-3-(6-methoxyquinolin-4-yl)propyl]-1-[2-(2,5-di-fluorophenylthio)ethyl]piperidine-3-acetic acid (3R,4R)-4-[3-(R,S)-Dimethylamino-3-(6-methoxyquinolin-4-yl)propyl]-1-[2-(3,5-di-fluorophenylthio)ethyl]piperidine-3-acetic acid (3R,4R)-4-[3-(R,S)-Dimethylamino-3-(6-methoxyquinolin-4-yl)propyl]-1-[2-(cyclo-pentylthio)ethyl]piperidine-3-acetic acid (3R,4R)-4-[3-(R,S)-Dimethylamino-3-(6-methoxyquinolin-4-yl)propyl]-1-[2-(cyclo-hexylthio)ethyl]piperidine-3-acetic acid (3R,4R)-4-[3-(R,S)-Dimethylamino-3-(6-methoxyquinolin-4-yl)propyl]-1-[2-(thien-2-yl)thioethyl]piperidine-3-acetic acid (3R,4R)-4-[3-(R,S)-Dimethylamino-3-(6-methoxyquinolin-4-yl)propyl]-1-[2-(1,3-thiazol-2-yl)thioethyl]piperidine-3-acetic acid (3R,4R)-4-[3-(R,S)-Dimethylamino-3-(6-methoxyquinolin-4-yl)propyl]-1-[2-(pyridin-2-yl)thioethyl]piperidine-3-acetic acid (3R,4R)-4-[3-(R,S)-Dimethylamino-3-(6-methoxyquinolin-4-yl)propyl]-1-[3-(3,5-di-fluorophenyl)prop-2-ynyl]piperidine-3-acetic acid (3R,4R)-4-[3-(R,S)-Dimethylamino-3-(6-methoxyquinolin-4-yl)propyl]-1-[3-(2,3,5-tri-fluorophenyl)prop-2-ynyl]piperidine-3-acetic acid (3R,4R)-4-[3-(R,S)-Dimethylamino-3-(6-methoxyquinolin-4-yl)propyl]-1-[3-(thien-2-yl)prop-2-ynyl]piperidine-3-acetic acid (3R,4R)-4-[3-(R,S)-Hydroxyamino-3-(6-methoxyquinolin-4-yl)propyl]-1-[2-(2,5-di-fluorophenylthio)ethyl]piperidine-3-acetic acid (3R,4R)-4-[3-(R,S)-Hydroxyamino-3-(6-methoxyquinolin-4-yl)propyl]-1-[2-(3,5-di-fluorophenylthio)ethyl]piperidine-3-acetic acid (3R,4R)-4-[3-(R,S)-Hydroxyamino-3-(6-methoxyquinolin-4-yl)propyl]-1-[2-(cyclo-phenylthio)ethyl]piperidine-3-acetic acid (3R,4R)-4-[3-(R,S)-Hydroxyamino-3-(6-methoxyquinolin-4-yl)propyl]-1-[2-(cyclo-hexylthio)ethyl]piperidine-3-acetic acid (3R,4R)-4-[3-(R,S)-Hydroxyamino-3-(6-methoxyquinolin-4-yl)propyl]-1-[2-(thien-2-yl)thioethyl]piperidine-3-acetic acid (3R,4R)-4-[3-(R,S)-Hydroxyamino-3-(6-methoxyquinolin-4-yl)propyl]-1-[2-(1,3-thiazol-2-yl)thioethyl]piperidine-3-acetic acid (3R,4R)-4-[3-(R,S)-Hydroxyamino-3-(6-methoxyquinolin-4-yl)propyl]-1-[2-(pyridin-2-yl)thioethyl]piperidine-3-acetic acid (3R,4R)-4-[3-(R,S)-Hydroxyamino-3-(6-methoxyquinolin-4-yl)propyl]-1-[3-(3,5-fluorophenyl)prop-2-ynyl]piperidine-3-acetic acid (3R,4R)-4-[3-(R,S)-Hydroxyamino-3-(6-methoxyquinolin-4-yl)propyl]-1-[3-(2,3,5-tri-fluorophenyl)prop-2-ynyl]piperidine-3-acetic acid (3R,4R)-4-[3-(R,S)-Hydroxyamino-3-(6-methoxyquinolin-4-yl)propyl]-1-[3-(thien-2-ynyl] piperidine-3-acetic acid (3R,4R)-4-[3-(R,S)-Methoxyamino-3-(6-methoxyquinolin-4-yl)propyl]-1-[2-(2,5-di-fluorophenylthio)ethyl]piperidine-3-acetic acid (3R,4R)-4-[3-(R,S)-Methoxyamino-3-(6-methoxyquinolin-4-yl)propyl]-1-[2-(3,5-fluorophenylthio)ethyl]piperidine-3-acetic acid (3R,4R)-4-[3-(R,S)-Methoxyamino-3-(6-methoxyquinolin-4-yl)propyl]-1-[2-(cyclo-phenylthio)ethyl]piperidine-3-acetic acid (3R,4R)-4-[3-(R,S)-Methoxyamino-3-(6-methoxyquinolin-4-yl)propyl]-1-[2-(cyclo-hexylthio)ethyl]piperidine-3-acetic acid (3R,4R)-4-[3-(R,S)-Methoxyamino-3-(6-methoxyquinolin-4-yl)propyl]-1-[2-(thien-2-yl)thioethyl]piperidine-3-acetic acid (3R,4R)-4-[3-(R,S)-Methoxyamino-3-(6-methoxyquinolin-4-yl)propyl]-1-[2-(1,3-thiazol-2-yl)thioethyl]piperidine-3-acetic acid (3R,4R)-4-[3-(R,S)-Methoxyamino-3-(6-methoxyquinolin-4-yl)propyl]-1-[2-(pyridin-2-yl)thioethyl]piperidine-3-acetic acid (3R,4R)-4-[3-(R,S)-Methoxyamino-3-(6-methoxyquinolin-4-yl)propyl]-1-[3-(3,5-di-fluorophenyl)prop-2-ynyl]piperidine-3-acetic acid (3R,4R)-4-[3-(R,S)-Methoxyamino-3-(6-methoxyquinolin-4-yl)propyl]-1-[3-(2,3,5-tri-fluorophenyl)prop-2-ynyl]piperidine-3-acetic acid (3R,4R)-4-[3-(R,S)-Methoxyamino-3-(6-methoxyquinolin-4-yl)propyl]-1-[3-(thien-2-yl)prop-2-ynyl]piperidine-3-acetic acid (3R,4R)-3-Hydroxymethyl-4-[3-(R,S)-amino-3-(6-methoxyquinolin-4-yl)propyl]-1-[2-(2,5-difluorophenylthio)ethyl]piperidine (3R,4R)-3-Hydroxymethyl-4-[3-(R,S)-amino-3-(6-methoxyquinolin-4-yl)propyl]-1-[2-(3,5-difluorophenylthio)ethyl]piperidine (3R,4R)-3-Hydroxymethyl-4-[3-(R,S)-amino-3-(6-methoxyquinolin-4-yl)propyl]-1-[2-(cyclopentylthio)ethyl]piperidine (3R,4R)-3-Hydroxymethyl-4-[3-(R,S)-amino-3-(6-methoxyquinolin-4-yl)propyl]-1-[2-(cyclohexylthio)ethyl]piperidine (3R,4R)-3-Hydroxymethyl-4-[3-(R,S)-amino-3-(6-methoxyquinolin-4-yl)propyl]-1-[2-(thien-2-yl)thioethyl]piperidine (3R,4R)-3-Hydroxymethyl-4-[3-(R,S)-amino-3-(6-methoxyquinolin-4-yl)propyl]-1-[2-(1,3-thiazol-2-yl)thioethyl]piperidine (3R,4R)-3-Hydroxymethyl-4-[3-(R,S)-amino-3-(6-methoxyquinolin-4-yl)propyl]-1-[2-pyridin-2-yl)thioethyl]piperidine (3R,4R)-3-Hydroxymethyl-4-[3-(R,S)-amino-3-(6-methoxyquinolin-4-yl)propyl]-1-[3-(3,5-difluorophenyl)prop-2-ynyl]piperidine (3R,4R)-3-Hydroxymethyl-4-[3-(R,S)-amino-3-(6-methoxyquinolin-4-yl)propyl]-1-[3-(2,3,5-trifluorophenyl)prop-2-ynyl]piperidine (3R,4R)-3-Hydroxymethyl-4-[3-(R,S)-amino-3-(6-methoxyquinolin-4-yl)propyl]-1-[3-(thien-2-yl)prop-2-ynyl]piperidine (3R,4R)-3-Hydroxymethyl-4-[3-(R,S)-methylamino-3-(6-methoxyquinolin-4-yl)propyl]-1-[2-(2,5-difluorophenylthio)ethyl]piperidine (3R,4R)-3-Hydroxymethyl-4-[3-(R,S)-methylamino-3-(6-methoxyquinolin-4-yl)propyl]-1-[2-(3,5-difluorophenylthio)ethyl]piperidine (3R,4R)-3-Hydroxymethyl-4-[3-(R,S)-methylamino-3-(6-methoxyquinolin-4-yl)propyl]-1-[2-(cyclopentylthio)ethyl]piperidine (3R,4R)-3-Hydroxymethyl-4-[3-(R,S)-methylamino-3-(6-methoxyquinolin-4-yl)propyl]-1-[2-(cyclohexylthio)ethyl]piperidine (3R,4R)-3-Hydroxymethyl-4-[3-(R,S)-methylamino-3-(6-methoxyquinolin-4-yl)propyl]-1-[2-(thien-2-yl)thioethyl]piperidine (3R,4R)-3-Hydroxymethyl-4-[3-(R,S)-methylamino-3-(6-methoxyquinolin-4-yl)propyl]-1-[2-(1,3-thiazol-2-yl)thioethyl]piperidine (3R,4R)-3-Hydroxymethyl-4-[3-(R,S)-methylamino-3-(6-methoxyquinolin-4-yl)propyl]-1-[2-(pyridin-2-yl)thioethyl]piperidine (3R,4R)-3-Hydroxymethyl-4-[3-(R,S)-methylamino-3-(6-methoxyquinolin-4-yl)propyl]-1-[3-(3,5-difluorophenyl)prop-2-ynyl]piperidine (3R,4R)-3-Hydroxymethyl-4-[3-(R,S)-methylamino-3-(6-methoxyquinolin-4-yl)propyl]-1-[3-(2,3,5-trifluorophenyl)prop-2-ynyl]piperidine (3R,4R)-3-Hydroxymethyl-4-[3-(R,S)-methylamino-3-(6-methoxyquinolin-4-yl)propyl]-1-[3-(thien-2-yl)prop-2-ynyl]piperidine (3R,4R)-3-Hydroxymethyl-4-[3-(R,S)-methylamino-3-(6-methoxyquinolin-4-yl)propyl]-1-[2-(2,5-difluorophenylthio)ethyl]piperidine (3R,4R)-3-Hydroxymethyl-4-[3-(R,S)-dimethylamino-3-(6-methoxyquinolin-4-yl)propyl]-1-[2-(3,5-difluorophenylthio)ethyl]piperidine (3R,4R)-3-Hydroxymethyl-4-[3-(R,S)-dimethylamino-3-(6-methoxyquinolin-4-yl)propyl]-1-[2-(cyclopentylthio)ethyl]piperidine (3R,4R)-3-Hydroxymethyl-4-[3-(R,S)-dimethylamino-3-(6-methoxyquinolin-4-yl)propyl]-1-[2-(cyclohexylthio)ethyl]piperidine (3R,4R)-3-Hydroxymethyl-4-[3-(R,S)-dimethylamino-3-(6-methoxyquinolin-4-yl)propyl]-1-[2-(thien-2-yl)thioethyl]piperidine (3R,4R)-3-Hydroxymethyl-4-[3-(R,S)-dimethylamino-3-(6-methoxyquinolin-4-yl)propyl]-1-[2-(1,3-thiazol-2-yl)thioethyl]piperidine (3R,4R)-3-Hydroxymethyl-4-[3-(R,S)-dimethylamino-3-(6-methoxyquinolin-4-yl)propyl]-1-[2-(pyridin-2-yl)thioethyl]piperidine (3R,4R)-3-Hydroxymethyl-4-[3-(R,S)-dimethylamino-3-(6-methoxyquinolin-4-yl)propyl]-1-[3-(3,5-difluorophenyl)prop-2-ynyl]piperidine (3R,4R)-3-Hydroxymethyl-4-[3-(R,S)-dimethylamino-3-(6-methoxyquinolin-4-yl)propyl]-1-[3-(2,3,5-trifluorophenyl)prop-2-ynyl]piperidine (3R,4R)-3-Hydroxymethyl-4-[3-(R,S)-dimethylamino-3-(6-methoxyquinolin-4-yl)propyl]-1-[3-(thien-2-yl)prop-2-ynyl]piperidine (3R,4R)-3-Hydroxymethyl-4-[3-(R,S)-hydroxyamino-3-(6-methoxyquinolin-4-yl)propyl]-1-[2-(2,5-difluorophenylthio)ethyl]piperidine (3R,4R)-3-Hydroxymethyl-4-[3-(R,S)-hydroxyamino-3-(6-methoxyquinolin-4-yl)propyl]-1-[2-(3,5-difluorophenylthio)ethyl]piperidine (3R,4R)-3-Hydroxymethyl-4-[3-(R,S)-hydroxyamino-3-(6-methoxyquinolin-4-yl)propyl]-1-[2-(cyclopentylthio)ethyl]piperidine (3R,4R)-3-Hydroxymethyl-4-[3-(R,S)-hydroxyamino-3-(6-methoxyquinolin-4-yl)propyl]-1-[2-(cyclohexylthio)ethyl]piperidine (3R,4R)-3-Hydroxymethyl-4-[3-(R,S)-hydroxyamino-3-(6-methoxyquinolin-4-yl)propyl]-1-[2-(thien-2-yl)thioethyl]piperidine (3R,4R)-3-Hydroxymethyl-4-[3-(R,S)-hydroxyamino-3-(6-methoxyquinolin-4-yl)propyl]-1-[2-(1,3-thiazol-2-yl)thioethyl]piperidine (3R,4R)-3-Hydroxymethyl-4-[3-(R,S)-hydroxyamino-3-(6-methoxyquinolin-4-yl)propyl]-1-[2-(pyridin-2-yl)thioethyl]piperidine (3R,4R)-3-Hydroxymethyl-4-[3-(R,S)-hydroxyamino-3-(6-methoxyquinolin-4-yl)propyl]-1-[2-(3,5-difluorophenyl)prop-2-ynyl]piperidine (3R,4R)-3-Hydroxymethyl-4-[3-(R,S)-hydroxyamino-3-(6-methoxyquinolin-4-yl)propyl]-1-[2-(2,3,5-trifluorophenyl)prop-2-ynyl]piperidine (3R,4R)-3-Hydroxymethyl-4-[3-(R,S)-hydroxyamino-3-(6-methoxyquinolin-4-yl)propyl]-1-[2-(thien-2-yl)prop-2-ynyl]piperidine (3R,4R)-3-Hydroxymethyl-4-[3-(R,S)-methoxyamino-3-(6-methoxyquinolin-4-yl)propyl]-1-[2-(2,5-difluorophenylthio)ethyl]piperidine (3R,4R)-3-Hydroxymethyl-4-[3-(R,S)-methoxyamino-3-(6-methoxyquinolin-4-yl)propyl]-1-[2-(3,5-difluorophenylthio)ethyl]piperidine (3R,4R)-3-Hydroxymethyl-4-[3-(R,S)-methoxyamino-3-(6-methoxyquinolin-4-yl)propyl]-1-[2-(cyclopentylthio)ethyl]piperidine (3R,4R)-3-Hydroxymethyl-4-[3-(R,S)-methoxyamino-3-(6-methoxyquinolin-4-yl)propyl]-1-[2-(cyclohexylthio)ethyl]piperidine (3R,4R)-3-Hydroxymethyl-4-[3-(R,S)-methoxyamino-3-(6-methoxyquinolin-4-yl)propyl]-1-[2-(thien-2-yl)thioethyl]piperidine (3R,4R)-3-Hydroxymethyl-4-[3-(R,S)-methoxyamino-3-(6-methoxyquinolin-4-yl)propyl]-1-[2-(1,3-thiazol-2-yl)thioethyl]piperidine (3R,4R)-3-Hydroxymethyl-4-[3-(R,S)-methoxyamino-3-(6-methoxyquinolin-4-yl)propyl]-1-[2-(pyridin-2-yl)thioethyl]piperidine (3R,4R)-3-Hydroxymethyl-4-[3-(R,S)-methoxyamino-3-(6-methoxyquinolin-4-yl)propyl]-1-[3-(3,5-difluorophenyl)prop-2-ynyl]piperidine (3R,4R)-3-Hydroxymethyl-4-[3-(R,S)-methoxyamino-3-(6-methoxyquinolin-4-yl)propyl]-1-[3-(2,3,5-trifluorophenyl)prop-2-ynyl]piperidine (3R,4R)-3-Hydroxymethyl-4-[3-(R,S)-methoxyamino-3-(6-methoxyquinolin-4-yl)propyl]-1-[3-(thien-2-yl)prop-2-ynyl]piperidine and their salts.

The following examples, presented without implied limitation, illustrate the present invention.

EXAMPLE 1

(3R,4R)-1-[3-(2,3,5-Trifluorophenyl)prop-2-ynyl]-4-[3-(R,S)-amino-3-(6-methoxyquinolin-4-yl)propyl]piperidine-3-carboxylic acid.

1.37 cm³ of 5N aqueous sodium hydroxide solution are added with stirring, at a temperature in the region of 20° C., to a solution of 0.9 g of methyl (3R,4R)-1-[3-(2,3,5-trifluorophenyl)prop 2-ynyl]-4-[3-(R,S)-amino-3-(6-methoxyquinolin-4-yl)propyl]piperidine-3-carboxylate in 9 cm³ of dioxane and then the combined mixture is brought to a temperature in the region of 60° C. for 16 hours. The mixture is concentrated under reduced pressure (5 kPa) at a temperature in the region of 40° C. The residue obtained is purified by chromatography at atmospheric pressure on a column of silica gel (particle size 20–45µ; mass 40 g), elution being carried out with a dichloromethane/methanol (90/10 by volume) mixture, a dichloromethane/methanol (80/20 by volume) mixture, a dichloromethane/methanol (60/40 by volume) mixture and a dichloromethane/methanol/triethylamine (74/25/1 by volume) mixture, with 100-cm³ fractions being collected Fractions 16 to 29 (which contain the purified product) are combined and then concentrated to dryness under the above conditions. The residue obtained is taken up in 30 cm³ of isopropyl ether, filtered off, washed 2 times with 20 cm³ of diethyl ether and then purified by chromatography at atmospheric pressure on a column of silica gel (particle size 20–45µ; diameter 2.3 cm; mass 25 g), elution being carried out with a dichloromethane/methanol (95/05 by volume) mixture. Fractions 4 to 7 are combined and then concentrated to dryness under the above conditions. The solid obtained is taken up in 25 cm³ of isopropyl ether, filtered off, washed 3 times with 10 cm³ of pentane and dried to afford 0.304 g of (3R,4R)-1-[3-(2,3,5-trifluorophenyl)prop-2-ynyl]-4-[3-(R,S)-amino-3-(6-methoxyquinolin-4-yl)propyl]piperidine-3-carboxylic acid.

$^1$H NMR spectrum (300 MHz, (CD$_3$)$_2$SO, δ in ppm). A mixture of diastereoisomers in the proportions 50/50 is observed.

From δ 1.35 to 1.90 (mt, 7H), from 2.35 to 2.90 (mt, 5H), 3.62 and 3.64 (2 s, 2H in total), 3.90 and 3.93 (2 s, 3H in total), from 4.55 to 4.70 (mt, 1H), 7.31 (mt, 1H), from 7.35 to 7.50 (mt, 2H), 7.59 and 7.62 (2 d, J=4.5 Hz, 1H in total), from 7.60 to 7.70 (mt, 1H), 7.92 and 7.94 (2 d, J=9 Hz, 1H in total), 8.68 and 8.70 (2 d, J=4.5 Hz, 1H in total).

$$[\alpha]_D^{20} = -9.5° \pm 0.4° (\text{at } 0.5\% \text{ in methanol})$$

Methyl (3R,4R)-1-[3-(2,3,5-trifluorophenyl)prop-2-ynyl]-4-[3-(R,S)-amino-3-(6-methoxyquinolin-4-yl)propyl]piperidine-3-carboxylate.

1.44 g of sodium borohydride and 0.77 g of molybdenum oxide are added with stirring and under an inert atmosphere, at a temperature in the region of –5° C., to a solution of 2.05 g of methyl (3R,4R)-1-[3-(2,3,5-trifluorophenyl)prop-2-ynyl]-4-[3-hydroxyimino-3-(6-methoxyquinolin-4-yl)propyl]piperidine-3-carboxylate in 100 cm³ of methanol. After 5 hours at a temperature in the region of 20° C., the mixture is concentrated under reduced pressure (5 kPa) at a temperature in the region of 40° C. The residue is purified by chromatography at atmospheric pressure on a column of silica gel (particle size 20-45µ; mass 30 g), elution being carried out with a dichloromethane/methanol/triethylamine (89/10/1 by volume) mixture. Fractions 3 to 5 (containing the purified product) are combined and then concentrated to dryness under the above conditions. 0.9 g of methyl (3R,4R)-1-[3-(2,3,5-trifluorophenyl)prop-2-ynyl]-4-[3-(R,S)-amino-3-(6-methoxyquinolin-4-yl)propyl]piperidine-3-carboxylate is obtained.

$^1$H NMR spectrum (300 MHz, (CD$_3$)$_2$SO, δ in ppm). A mixture of diastereoisomers in the proportions 50/50 is observed.

From δ 1.20 to 1.90 (mt, 7H), from 2.10 to 2.90 (mt, 5H), 3.47 and 3.50 (2 s, 3H in total), 3.58 and 3.59 (2 s, 2H in total), 3.92 and 3.93 (2 s, 3H in total), from 4.50 to 4.65 (mt, 1H), 7.31 (mt, 1H), from 7.35 to 7.50 (mt, 2H), from 7.60 to 7.70 (mt, 1H), 7.60 and 7.61 (2 d, J=4.5 Hz, 1H in total), 7.93 and 7.94 (2 d, J=9 Hz, 1H in total), 8.69 and 8.70 (2 d, J=4.5 Hz, 1H in total).

Methyl (3R,4R)-1-[3-(2,3,5-trifluorophenyl)prop-2-ynyl]-4-[3-hydroxyimino-3-(6-methoxyquinolin-4-yl)propyl]piperidine-3-carboxylate.

0.834 g of hydroxylamine hydrochloride is added, with stirring and under an inert atmosphere, to a mixture of 3.5 g of methyl (3R,4R)-1-[3-(2,3,5-trifluorophenyl)prop-2-ynyl]-4-[3oxo-3-(6-methoxyquinolin-4-yl)propyl]piperidine-3-carboxylate in 35 cm³ of pyridine at a temperature in the region of 20° C. The mixture is stirred for 5 hours at a temperature in the region of 20° C. The reaction mixture is concentrated to dryness under reduced pressure (5 kPa) at a temperature in the region of 40° C. The residue is taken up in 300 cm³ of ethyl acetate and 100 cm³ of water. After standing for 16 hours, the mixture is extracted with 3 times 100 cm³ of ethyl acetate. The organic extracts are combined, washed with 3 times 100 cm³ of water, dried over sodium sulfate, filtered and concentrated to dryness under reduced pressure (5 kPa) at a temperature in the region of 40° C. 3.35 g of methyl (3R,4R)-1-[3-(2,3,5-trifluorophenyl)prop-2-ynyl]-4-[3-hydroxyimino-3-(6-methoxyquinolin-4-yl)propyl]piperidine-3-carboxylate are obtained.

$^1$H NMR spectrum (300 MHz, (CD$_3$)$_2$SO, δ in ppm). A mixture of the two Z and E isomers in the proportions 60/40 or 40/60 is observed.

From δ 1.30 to 1.90 (mt, 5H), from 2.25 to 3.00 (mt, 7H), 3.35 and 3.41 (2 s, 3H in total), 3.57 and 3.58 (2 s, 2H in total), 3.84 and 3.87 (2 s, 3H in total), from 7.20 to 7.70 (mt, 4H), 6.89 and 7.50 (2 d, J=4.5 Hz, 1H in total), 7.97 and 7.98 (2 d, J=9 Hz, 1H in total), 8.76 and 8.77 (2 d, J=4.5 Hz, 1H in total), 10.86 and 11.63 (2 s, 1H in total).

Methyl (3R,4R)-1-[3-(2,3,5-trifluorophenyl)prop-2-ynyl]-4-[3-oxo-3-(6-methoxyquinolin-4-yl)propyl]piperidine-3-carboxylate.

4.05 g of tetrakis(triphenylphosphine)palladium, 0.834 g of cuprous iodide and 7.9 cm³ of 1-bromo-2,3,5-trifluorobenzene are added at a temperature in the region of 20° C., with stirring and under an inert atmosphere, to a solution of 17.28 g of methyl (3R,4R)-1-(3-prop-2-ynyl)-4-[3-oxo-3-(6-methoxyquinolin-4-yl)propyl]piperidine-3-carboxylate in 173 cm³ of triethylamine. After heating for 2 hours at a temperature in the region of 80° C., the reaction mixture is cooled to approximately 20° C., diluted with 100 cm³ of water and then extracted with 4 times 150 cm³ of ethyl acetate. The organic extracts are combined, washed with 5 times 100 cm³ of water, dried over sodium sulfate, filtered and concentrated under reduced pressure (1 kPa) at a temperature in the region of 50° C. The residue is purified by chromatography at atmospheric pressure on a column of silica gel (particle size 20-45µ; diameter 7 cm; mass 600 g), elution being carried out with ethyl acetate. Fractions 3 to 11 are combined and then concentrated under the above conditions. 18.4 g of methyl (3R,4R)-1-[3-(2,3,5-trifluorophenyl)prop-2-ynyl]-4-[3-oxo-3-(6-methoxyquinolin-4-yl)propyl]piperidine-3-carboxylate are obtained.

¹H NMR spectrum (400 MHz, (CD₃)₂SO, δ in ppm): from δ 1.55 to 1.95 (mt, 5H), 2.39 (mt, 1H), 2.58 (broad d, J=10 Hz, 1H), 2.68 (mt, 1H), 2.82 (mt, 1H), 2.91 (mt, 1H), 3.09 (mt, 1H), 3.23 (mt, 1H), 3.58 (s, 3H), 3.61 (s, 2H), 3.88 (s, 3H), 7.31 (mt, 1H), 7.49 (dd, J=9 and 2.5 Hz, 1H), from 7.55 to 7.65 (mt, 1H), 7.73 (d, J=2.5 Hz, 1H), 7.92 (d, J=4.5 Hz, 1H), 8.02 (d, J=9 Hz, 1H), 8.89 (d, J=4.5 Hz, 1H).

Methyl (3R,4R)-1-(3-prop-2-ynyl)-4-[3-oxo-3-(6-methoxyquinolin-4-yl)propyl]piperidine-3-carboxylate.

23.7 cm³ of triethylamine and 6.35 cm³ of propargyl bromide are added at a temperature in the region of 20° C., with stirring and under an inert atmosphere, to a solution of 14.43 g of methyl (3R,4R)-4-[3-oxo-3-(6-methoxyquinolin-4-yl)propyl]piperidine-3-carboxylate in 350 cm³ of anhydrous dimethylformamide. After heating for 5 hours at a temperature in the region of 45° C., the reaction mixture is cooled to approximately 20° C., poured into 190 cm³ of water and 190 cm³ of ethyl acetate, and then extracted with 3 times 250 cm³ of ethyl acetate. The organic extracts are combined, washed 3 times with 250 cm³ of water, dried over sodium sulfate, filtered and concentrated under reduced pressure (1 kPa) at a temperature in the region of 50° C. The residue is purified by chromatography at atmospheric pressure on a column of silica gel (particle size 20–45µ; diameter 8 cm; mass 600 g), elution being carried out with ethyl acetate and an ethyl acetate/methanol (95/05 by volume) mixture and 400-cm³ fractions being collected. Fractions 3 to 13 are combined and then concentrated under the above conditions. 17.5 g of methyl (3R,4R)-1-(3-prop-2-ynyl)-4-[3-oxo-3-(6-methoxyquinolin-4-yl)propyl]piperidine-3-carboxylate are obtained.

¹H NMR spectrum (300 MHz, (CD₃)₂SO, δ in ppm): from δ 1.55 to 1.95 (mt, 5H), 2.30 (mt, 1H), from 2.45 to 2.65 (mt, 2H), 2.79 (mt, 2H), from 3.00 to 3.35 (mt, 2H), 3.17 (t, J=2.5 Hz, 1H), 3.27 (d, J=2.5 Hz, 2H), 3.57 (s, 3H), 3.90 (s, 3H), 7.50 (dd, J=9 and 2.5 Hz, 1H). (d, J=2.5 Hz, 1H), 7.93 (d, J=4.5 Hz, 1H), 8.03 (d, J=9 Hz, 1H), 8.90 (d, J =4.5 Hz, 1H).

Methyl (3R,4R)-4-[3-oxo-3-(6-methoxyquinolin-4-yl) propyl]piperidine-3-carboxylate can be prepared in the following way:

A solution of 19.4 g of (3R,4R)-4-[3-oxo-3-(6-methoxyquinolin-4-yl)propyl]-1-(t-butyloxycarbonyl) piperidine-3-carboxylic acid (80% content) in 355 cm³ of methanol is cooled to a temperature in the region of −30° C. Thionyl chloride (7.7 cm³)is added with stirring while maintaining the temperature between −25 and −30° C. After the addition, the mixture is maintained in the vicinity of −30° C. for 30 minutes and then the temperature is allowed to return to the vicinity of 20° C. After stirring at ambient temperature for 19 hours, the reaction mixture is concentrated under reduced pressure (5 kPa) at a temperature in the region of 30° C. The residue is taken up in 300 cm³ of water to which 200 cm³ of dichloromethane have been added, and then stirred. The organic phase is separated by settling; the aqueous phase is again extracted with 200 cm³ of dichloromethane. The aqueous solution is brought to pH 8 by gradual addition of solid sodium hydrogen carbonate. After extracting the alkaline solution 3 times with 200 cm³ of dichloromethane, the combined organic extracts are washed 2 times with 200 cm³ of water and then dried over magnesium sulfate. After filtering through a paper filter, the organic solution is concentrated under reduced pressure (5 kPa) at a temperature in the region of 40° C. to afford 4.51 g of methyl (3R,4R)-4-[3-oxo-3-(6-methoxyquinolin-4-yl)propyl] piperidine-3-carboxylate.

(3R,4R)-4-[3-Oxo-3-(6-methoxyquinolin-4-yl)propyl]-1-(tert-butoxycarbonyl)piperidine-3-carboxylic acid can be prepared in the following way:

A solution of 36 g of (3R,4R)-4-[3-oxo-3-(6-methoxyquinolin-4-yl)propyl]-3-vinylpiperidine in 54 cm³ of acetone is cooled to a temperature in the region of 0° C. 150 cm³ of 3M sulfuric acid are added over 15 minutes with stirring while maintaining the temperature between 0 and 5° C. The temperature is lowered to the vicinity of 0° C. and a solution of 32 g of sodium permanganate in 200 cm³ of distilled water is added dropwise to the mixture. The reaction mixture is stirred for an additional 45 minutes at a temperature of between 10 and 15° C. and then the temperature is allowed to rise to the vicinity of 20° C. After stirring for 3 hours at this temperature, the reaction mass is cooled to a temperature in the region of 0° C. and then 160 cm³ of 38% potassium hydroxide solution are slowly added at a temperature of less than 10° C. After stirring for 30 minutes at a temperature in the region of 10° C., the mixture is filtered. The filter cake is taken up in 300 cm³ of water to which 15 cm³ of 38% potassium hydroxide solution have been added, and stirred for 20 minutes. After filtering and then washing the filter cake 2 times with 200 cm³ of distilled water, the filtrates are combined and then 24 g of di(tert-butyl) dicarbonate are added thereto. The solution is stirred at a temperature in the region of 20° C. for 15 hours. After addition of 1 liter of ethyl acetate and stirring, the mixture is allowed to settle, the aqueous phase is separated and then brought to pH 5 by addition of 38 cm³ of 37% concentrated aqueous hydrochloric acid. The mixture is again extracted 5 times with 1 liter of ethyl acetate. The extracts are combined and then washed 2 times with 1 liter of water saturated with sodium chloride. The organic solution is dried over magnesium sulfate, filtered through a paper filter and concentrated under reduced pressure (5 kPa) at a temperature in the region of 40° C. to afford 21.2 g of (3R,4R)-4-[3-oxo-3-(6-methoxyquinolin-4-yl)propyl]-1-(t-butyloxycarbonyl) piperidine-3-carboxylic acid in the form of a brown solid melting at 114° C.

(3R,4R)-4-[3-Oxo-3-(6-methoxyquinolin-4-yl)propyl]-3-vinylpiperidine can be obtained by the application of the method disclosed in patent application FR 2 354 771.

EXAMPLE 2

(3R,4R)-1-[2-(Thien-2-ylthio)ethyl]-4-[3-(R,S)-amino-3-(6-methoxyquinolin-4-yl)-propyl]piperidine-3-carboxylic acid, sodium salt.

1 cm$^3$ of 5N aqueous sodium hydroxide solution is added with stirring, at a temperature in the region of 20° C., to a solution of 0.05 g of methyl (3R,4R)-1-[2-(thien-2-ylthio)ethyl]-4-[3-(R,S)-amino-3-(6-methoxyquinolin-4-yl)propyl]piperidine-3-carboxylate in 2 cm$^3$ of dioxane and 2 cm$^3$ of methanol, and then the combined mixture is brought to reflux and refluxed for 20 hours. The mixture is concentrated under reduced pressure (5 kPa) at a temperature in the region of 40° C. The residue obtained is dissolved in 6 cm$^3$ of distilled water The aqueous phase is washed with 2 cm$^3$ of methylene chloride and then evaporated to dryness. The residue is taken up in 2 cm$^3$ of isopropanol and the insoluble material is washed with 2 cm$^3$ of isopropanol and then dried to give 0.05 g of (3R,4R)-1-[2-(thien-2-ylthio)ethyl]-4-[3-(R,S)-amino-3-(6-methoxyquinolin-4-yl)propyl]piperidine-3-carboxylic acid, sodium salt.

$^1$H NMR spectrum (300 MHz, (CD$_3$)$_2$SO, δ in ppm): A mixture of diastereoisomers is observed.

From δ 1.15 to 2.85 (mts, 14H), 2.92 (mt, 2H), from 3.90 to 4.00 (mt, 3H in total), from 4.45 to 4.70 (mt, 1H), 7.06 (mt, 1H), 7.19 (mt, 1H), from 7.30 to 7.50 (mt, 2H), from 7.55 to 7.65 (mt, 2H), 7.93 (d, J=9 Hz, 1H), 8.69 (mt, 1H).

Methyl (3R,4R)-1-[2-(thien-2-ylthio)ethyl]-4-[3-(R,S)-amino-3-(6-methoxyquinolin-4-yl)propyl]piperidine-3-carboxylate.

0.125 g of sodium borohydride and 0.066 g of molybdenum oxide are added with stirring and under an inert atmosphere, at a temperature in the region of −5° C., to a solution of 0.17 g of methyl (3R,4R)-1-[2-(thien-2-ylthio)ethyl]-4-[3-hydroxyimino-3-(6-methoxyquinolin-4-yl)propyl]piperidine-3-carboxylate in 10 cm$^3$ of methanol. After 5 hours at a temperature in the region of 20° C., 0.125 g of sodium borohydride and 0.066 g of molybdenum oxide are again added and then the reaction mixture is stirred for an additional 18 hours at a temperature in the region of 20° C. The resulting mixture is concentrated under reduced pressure (5 kPa) at a temperature in the region of 40° C. The residue obtained is purified by chromatography under a pressure of 50 kPa of nitrogen on a column of silica gel (particle size 20–45 μ; mass 34 g; diameter of the column 2.3 cm), elution being carried out with a dichloromethane/methanol (95/5 by volume) mixture. Fractions 220 to 365 (containing the purified product) are combined and then concentrated to dryness under the above conditions to afford 0.06 g of methyl (3R,4R)-1-[2-(thien-2-ylthio)ethyl]-4-[3-(R,S)-amino-3-(6-methoxyquinolin-4-yl)propyl]piperidine-3-carboxylate.

Mass spectrum: DCI m/z=499 MH$^+$ base peak

Methyl (3R,4R)-1-[2-(thien-2-ylthio)ethyl]-4-[3-hydroxyimino-3-(6-methoxyquinolin-4-yl)propyl]piperidine-3-carboxylate.

0.32 g of hydroxylamine hydrochloride is added, with stirring and under an inert atmosphere, to a mixture of 1.27 g of methyl (3R,4R)-1-[2-(thien-2-ylthio)ethyl]-4-[3-oxo-3-(6-methoxyquinolin-4-yl)propyl]piperidine-3-carboxylate in 13 cm$^3$ of pyridine at a temperature in the region of 20° C. The mixture is stirred for 1 hour at a temperature in the region of 20° C. The resulting reaction mixture is diluted with 130 cm$^3$ of distilled water and the mixture thus obtained is extracted with 50 cm$^3$ of ethyl acetate and then two times with 30 cm$^3$ of ethyl acetate. The combined organic phases are washed two times with 50 cm$^3$ of distilled water, dried over magnesium sulfate and then concentrated to dryness under reduced pressure (5 kPa) at a temperature in the region of 40° C. The residue is purified by chromatography under a pressure of 50 kPa of nitrogen on a column of silica gel (particle size 20–45 μ; weight of silica 160 g, diameter of the column 3.5 cm), elution being carried out with a mixture of ethyl acetate and cyclohexane (90/10 by volume). Fractions 20 to 22 are combined and then concentrated to dryness under the above conditions. 0.1 g of methyl (3R,4R)-1-[2-(thien-2-ylthio)ethyl]-4-[3-hydroxyimino-3-(6-methoxyquinolin-4-yl)propyl]piperidine-3-carboxylate is obtained.

Mass spectrum: DCI m/z=513 MH$^+$ base peak

Methyl (3R,4R)-1-[2-(thien-2-ylthio)ethyl]-4-[3-oxo-3-(6-methoxyquinolin-4-yl)-propyl]piperidine-3-carboxylate.

3.8 cm$^3$ of diisopropylethylamine and 1.54 g of 2-(2-bromoethylthio)thiophene are added at a temperature in the region of 20° C., with stirring and under an inert atmosphere, to a solution of 2.23 g of methyl (3R,4R)-4-[3-oxo-3-(6-methoxyquinolin-4-yl)propyl]piperidine-3-carboxylate hydrobromide in 350 cm$^3$ of anhydrous N-methylpyrrolidone. After heating for 3 hours at a temperature in the region of 60° C., the reaction mixture is cooled to approximately 20° C., poured onto 50 cm$^3$ of water; and 25 cm$^3$ of ethyl acetate are added. The mixture obtained is extracted 3 times with 25 cm$^3$ of ethyl acetate. The organic extracts are combined, washed twice with 50 cm$^3$ of distilled water and then extracted successively with 25 cm$^3$ of 1N aqueous HCl solution (the pH is brought to 2) and then with 25 cm$^3$ of distilled water. The aqueous phases are combined and the pH is brought to 9 by addition of 25 cm$^3$ of a 1N aqueous sodium hydroxide solution. The resulting aqueous phase is extracted with 50 cm$^3$ of ethyl acetate and then 3 times with 25 cm$^3$ of ethyl acetate. The organic phases are combined, washed with 50 cm$^3$ of distilled water and then dried over sodium sulfate, filtered and concentrated under reduced pressure (1 kPa) at a temperature in the region of 50° C. The residue is purified by chromatography under a pressure of 50 kPa of nitrogen on a column of silica gel (particle size 20–45 μ; diameter 3.4 cm; weight of silica 47 g), elution being carried out with an ethyl acetate/cyclohexane (60/40 by volume) mixture and 40-cm$^3$ fractions being collected. Fractions 8 to 42 are combined and then concentrated under the above conditions to afford 1.27 g of methyl (3R,4R)-1-[2-(thien-2-ylthio)ethyl]-4-[3-oxo-3-(6-methoxyquinolin-4-yl)propyl]piperidine-3-carboxylate in the form of a yellow oil.

Mass spectrum: DCI m/z=498 MH$^+$ base peak

The present invention also relates to pharmaceutical compositions comprising at least one quinolylpropylpiperidine derivative according to the invention, if appropriate in the form of a salt, in the pure state or in the form of a combination with one or more compatible and pharmaceutically acceptable diluents or adjuvants.

The compositions according to the invention can be used orally, parenterally, topically, rectally or in aerosols.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch. These compositions can comprise substances other than diluents, for example a lubricant, such as magnesium stearate, or a coating intended for controlled release.

Use may be made, as liquid compositions for oral administration, of pharmaceutically acceptable solutions, suspensions, emulsions, syrups and elixirs comprising inert diluents, such as water or liquid paraffin. These compositions can also comprise substances other than diluents, for example wetting, sweetening or other flavoring products.

The compositions for parenteral administration can be emulsions or sterile solutions. Use may be made, as solvent or vehicle, of water, propylene glycol, a polyethylene glycol, vegetable oils, in particular olive oil, or injectable organic esters, for example ethyl oleate. These compositions can also comprise adjuvants, in particular wetting, isotonizing, emulsifying, dispersing and stabilizing agents.

Sterilization can be carried out in several ways, for example using a bacteriological filter, by irradiation or by heating. They can also be prepared in the form of sterile solid compositions which can be dissolved at the time of use in sterile water or any other injectable sterile medium.

The compositions for topical administration can be, for example, creams, ointments, lotions or aerosols.

The compositions for rectal administration are suppositories or rectal capsules which comprise, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle with a particle size of 30 to 80 μm, for example dextran, mannitol or lactose.

In human therapeutics, the novel quinolylpropylpiperidine derivatives according to the invention are of particular use in the treatment of infections of bacterial origin. The doses depend on the desired effect and on the duration of the treatment. The physician will determine the dosage which he considers the most appropriate according to the treatment and according to the age, weight, stage of the infection and other factors specific to the subject to be treated. The doses are generally between 750 mg and 3 g of active product taken 2 or 3 times per day orally or between 400 mg and 1.2 g intravenously for an adult.

The following example illustrates a composition according to the invention.

A liquid composition intended for parenteral use is prepared according to the usual technique; it comprises:

| | | | |
|---|---|---|---|
| (3R,4R)-1-[3-(2,3,5-Trifluorophenyl)prop-2-ynyl]-4-[3-(R,S)-amino-3-(6-methoxyquinolin-4-yl)-propyl]piperidine-3-carboxylic acid | | | 125 mg |
| Glucose | q.s. | for | 2.5% |
| Sodium hydroxide | q.s. | for | pH = 4–4.5 |
| Water for Injections | | | q.s. for 20 ml |

What is claimed is:
1. A quinolylpropylpiperidine derivative of general formula:

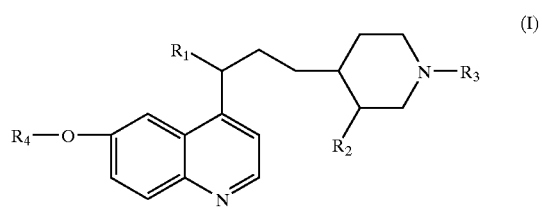

in which:

$R_1$ is an amino, alkylamino, dialkylamino, hydroxyamino, alkyloxyamino, or alkyl(alkyloxy)amino radical, $R_2$ is a carboxyl, carboxymethyl or hydroxymethyl radical, $R_3$ is an alkyl radical having 1 to 6 carbon atoms substituted by a substituent selected from the group consisting of a.) a phenylthio radical which, itself, has up to 4 substituents selected from the group consisting of halogen, hydroxyl, alkyl, alkyloxy, trifluoromethyl, trifluoromethoxy, carboxyl, alkyloxycarbonyl, cyano and amino, b.) a cycloalkylthio radical, the cyclic part of which comprises 3 to 7 members, and c.) a 5- to 6-membered heteroarylthio radical comprising 1 to 4 heteroatoms selected from the group consisting of nitrogen, oxygen and sulfur and optionally substituted by one or more substituents selected from the group consisting of halogen, hydroxyl, alkyl, alkyloxy, trifluoromethyl, trifluoromethoxy, oxo, carboxyl, alkyloxycarbonyl, cyano and amino; or, alternatively, $R_3$ is a propargyl radical that is (a) substituted by a phenyl radical which is optionally substituted by 1 to 4 substituents selected from the group consisting of halogen, hydroxyl, alkyl, alkyloxy, trifluoromethyl, trifluoromethoxy, carboxyl, alkyloxycarbonyl, cyano and amino or (b) substituted by a cycloalkyl radical comprising 3 to 7 members or (c) substituted by a 5- to 6-membered heteroaryl radical comprising 1 to 4 heteroatoms selected from the group consisting of nitrogen, oxygen and sulfur, said heteroaryl radical being optionally substituted by one or more substituents selected from the group consisting of halogen, hydroxyl, alkyl, alkyloxy, trifluoromethyl, trifluoromethoxy, oxo, carboxyl, alkyloxycarbonyl, cyano and amino, and $R_4$ is selected from the group consisting of an alkyl radical comprising 1 to 6 carbon atoms, an alkenyl-$CH_2$— radical, the alkenyl portion of which comprises 2 to 6 carbon atoms, an alkynyl-$CH_2$— radical, the alkynyl portion of which comprise 2 to 6 carbon atoms, a cycloalkyl radical, the cyclic portion of which comprises 3 to 8 members and a (cycloalkyl)alkyl radical, the cyclic portion of which comprises 3 to 8 members, said alkyl radicals being straight- or branched-chain radicals that, unless otherwise specified, comprise 1 to 4 carbon atoms, in its cis and trans forms and/or in its diastereoisomeric forms or their mixtures, and the pharmaceutically acceptable salts thereof.

2. A process for the preparation of a quinolylpropylpiperidine derivative as claimed in claim 1, which process comprises the following steps:

1) condensation of an $R_3$ chain as defined in claim 1 onto a quinolylpropylpiperidine derivative of general formula:

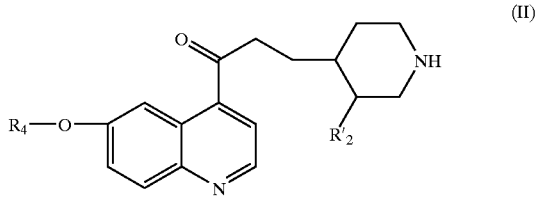
(II)

in which R₄ is as defined in claim 1 and R'₂ is a protected carboxyl radical or a protected carboxymethyl radical, whereby there is obtained a quinolylpropylpiperidine derivative of general formula:

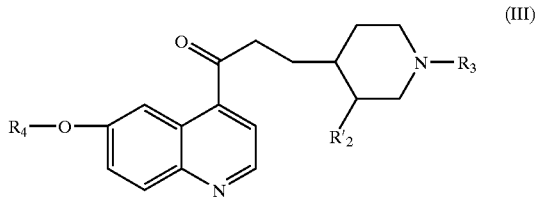
(III)

in which R'₂ and R₄ are as defined above and R₃ is as defined in claim 1;

2) conversion of the oxo radical to a hydroxyimino or alkyloxyimino radical, in order to obtain a quinolylpropylpiperidine derivative of general formula:

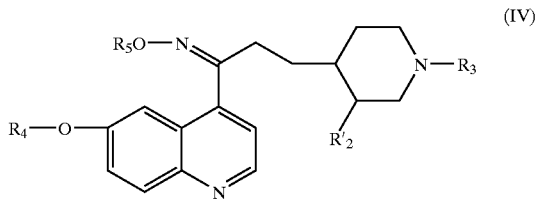
(IV)

in which R'₂, R₃ and R₄ are as defined above and R₅ is a hydrogen atom or an alkyl radical, 3) then, if appropriate, the reduction of the product of step 2) to an amine, and, optionally, the conversion to a monoalkylated or dialkylated amine, or the reduction to a hydroxylamine or to an alkyloxyamine, 4) then, if appropriate, the conversion of the derivative obtained from step 3) in which R₁ is alkyloxyamino to alkyl(alkyloxy)amino by alkylation, 5) then, the conversion of the R'₂ radical to a carboxyl or carboxymethyl radical, 6) then, if appropriate, the reduction of the carboxyl radical thus obtained or of the protected carboxyl radical which R'₂ may be to a hydroxymethyl radical and, 7) optionally, the conversion of the latter to a carboxymethyl radical according to the usual methods, and 8) optionally, the conversion of the product obtained to a pharmaceutically acceptable salt and/or, if appropriate, separation of its isomeric forms.

3. The process as claimed in claim 2, wherein the condensation of the R₃ chain onto the piperidine is carried out by the action of a derivative of general formula:

R₃—X       (V)

in which R₃ is as defined in claim 1 and X is a halogen atom, a methylsulfonyloxy radical, a trifluoromethylsulfonyloxy radical or a p-toluenesulfonyloxy radical.

4. The process as claimed in claim 3, wherein, when R₃ represents propargyl substituted by phenyl, cycloalkyl or heteroaryl as defined in claim 1, and the reaction is carried out by condensation of a propargyl halide and then substitution of the propargyl chain with a phenyl, cycloalkyl or heteroaryl radical.

5. A quinolylpropylpiperidine derivative, which corresponds to the general formula:

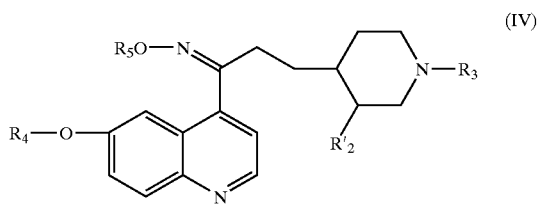
(IV)

in which R'₂, R₃ R₄ and R₅ are as defined in claim 2.

6. A quinolylpropylpiperidine derivative, which corresponds to the general formula:

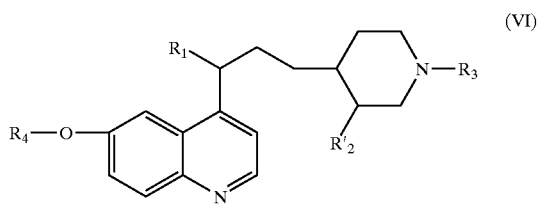
(VI)

in which R₁ is as defined in claim 1 and R'₂, R₃ and R₄ are as defined in claim 2.

7. A pharmaceutical composition, which comprises at least one compound as claimed in claim 1, in the pure state or in combination with one or more compatible and pharmaceutically acceptable diluents or adjuvants.

8. A method of treating microbial infections, which comprises administering to a patient in need thereof an antimicrobially effective amount of a pharmaceutical composition as claimed in claim 7.

* * * * *